(12) United States Patent
Kalbermatten et al.

(10) Patent No.: US 10,184,874 B2
(45) Date of Patent: Jan. 22, 2019

(54) APPARATUS FOR DISSOLUTION TESTING

(71) Applicant: Sotax AG, Aesch (CH)

(72) Inventors: Gilles Kalbermatten, Bartenheim (FR); Rolf Benz, Arlesheim (CH)

(73) Assignee: Sotax AG, Aesch (CH)

( * ) Notice: Subject to any disclaimer, the term of this patent is extended or adjusted under 35 U.S.C. 154(b) by 207 days.

(21) Appl. No.: 15/103,938

(22) PCT Filed: Dec. 5, 2014

(86) PCT No.: PCT/EP2014/076675
§ 371 (c)(1),
(2) Date: Jun. 13, 2016

(87) PCT Pub. No.: WO2015/086446
PCT Pub. Date: Jun. 18, 2015

(65) Prior Publication Data
US 2016/0327466 A1 Nov. 10, 2016

(30) Foreign Application Priority Data

Dec. 13, 2013 (CH) ...................................... 2066/13

(51) Int. Cl.
*G01N 13/00* (2006.01)
*G01N 33/15* (2006.01)
(Continued)

(52) U.S. Cl.
CPC ........... *G01N 13/00* (2013.01); *B01F 1/0038* (2013.01); *B01F 7/161* (2013.01);
(Continued)

(58) Field of Classification Search
CPC .. G01N 13/00; G01N 33/15; G01N 2013/006; G01N 2035/00198;
(Continued)

(56) References Cited

U.S. PATENT DOCUMENTS 1,345,593 A 7/1920 Giddens
3,811,780 A 5/1974 Liston
(Continued)

FOREIGN PATENT DOCUMENTS

EP 2306204 A1 4/2011

OTHER PUBLICATIONS

"DT-810 Dissolution Tester," Oct. 31, 2005, Retrieved from the Internet: URL:http://www.jascoinc.com/docs/product-brochures/dissolution-testers-dt-810-series.pdf.
(Continued)

*Primary Examiner* — Joseph G Ustaris
*Assistant Examiner* — Jill D Sechser
(74) *Attorney, Agent, or Firm* — Hammer & Associates, P.C.

(57) ABSTRACT

An apparatus (1) for dissolution testing comprises a tank (2) having a circular cylindrical outer body portion (21) with a transparent side wall and a circular cylindrical inner body portion (22) with a transparent side wall, wherein the inner body portion (22) is coaxially arranged with respect to the outer body portion (21) such that an outer interior (23) having a ring-shaped cross section is defined between the outer body portion (21) and the inner body portion (22) and an inner interior (24) having a circular cross section is defined inside the inner body portion. The apparatus (1) further comprises a plurality of dissolution vessels (4) arranged in the outer interior (23) of the tank and a heater assembly being arranged to heat a test media in the vessels (4) to a predefined temperature. The apparatus (1) according to the invention allows for a comparably precise monitoring of vessels (4) inside the tank (2) and/or an appropriate manipulation of the vessels (4) inside the tank (2).

15 Claims, 2 Drawing Sheets

(51) Int. Cl.
  *B01F 7/16* (2006.01)
  *B01F 13/10* (2006.01)
  *B01F 1/00* (2006.01)
  *H04N 5/225* (2006.01)
  *H04N 5/247* (2006.01)
  *G01N 35/00* (2006.01)

(52) U.S. Cl.
  CPC ......... *B01F 13/1022* (2013.01); *G01N 33/15* (2013.01); *H04N 5/2256* (2013.01); *H04N 5/247* (2013.01); *B01F 2215/0032* (2013.01); *G01N 2013/006* (2013.01); *G01N 2035/00198* (2013.01)

(58) Field of Classification Search
  CPC .... H04N 5/247; H04N 5/2256; B01F 1/0038; B01F 7/161; B01F 13/1022; B01F 2215/0032
  See application file for complete search history.

(56) References Cited

U.S. PATENT DOCUMENTS

| | | | |
|---|---|---|---|
| 4,200,607 A | 4/1980 | Suzuki | |
| 5,246,665 A | 9/1993 | Tyranski et al. | |
| 5,816,701 A | 10/1998 | Martin et al. | |
| 6,691,748 B1 | 2/2004 | Tajima | |
| 8,158,059 B2 | 4/2012 | Kennedy et al. | |
| 2006/0260422 A1* | 11/2006 | Sekizawa | G01N 33/15 73/866 |
| 2006/0260423 A1 | 11/2006 | Sekizawa et al. | |
| 2007/0196238 A1* | 8/2007 | Kennedy | G01N 13/00 422/68.1 |
| 2008/0223845 A1 | 9/2008 | Garr | |
| 2010/0314383 A1 | 12/2010 | Kollewe | |
| 2011/0216805 A1* | 9/2011 | Fernando | G01N 33/15 374/121 |
| 2012/0221252 A1* | 8/2012 | Heinz | G01N 21/6486 702/19 |

OTHER PUBLICATIONS

Youngchan Kim et al., "Measurement Techniques for Red Blood Cell Deformability: Recent Advances," Blood Cell—An Overview of Studies in Hematology, InTech, (p. 167-194), (Sep. 21, 2012).
Warren Groner et al., "New Optical Technique for Measuring Erythrocyte Deformability with the Ektacytometer," Clinical Chemistry, (vol. 26), (Issue. 10), (p. 1435-1442), (Sep. 1, 1980).

* cited by examiner

APPARATUS FOR DISSOLUTION TESTING

TECHNICAL FIELD

The present invention relates generally to the field of dissolution testing and more particular to an apparatus for testing dissolution of a sample.

BACKGROUND ART

Dissolution testing involves physical evaluation of solid dosage forms such as capsules and tablets. Results of dissolution testing are useful in studying drug release characteristics of the dosage form and evaluating equipment and processes used in forming individual doses. To ensure uniformity in testing, entities such as the United States Pharmacopeia (USP) and the European Pharmacopeia provide guidelines for equipment used in dissolution testing.

Under these guidelines, typically a capsule or tablet is deposited in a test vessel containing dissolution media intended to emulate, for example, stomach or intestinal fluids. The vessel is maintained at a constant temperature, and the vessel contents are agitated at a specified speed. Samples of the resulting solution are then taken at predetermined times and analyzed using techniques such as high performance liquid chromatography (HPLC) and spectral analysis.

Conventional dissolution testing systems include pumps and tubing for transferring the samples from the test vessels to the analytical equipment. The samples transferred using such an arrangement may be as large as 10 ml. One disadvantage of using such large-volume samples is that the samples may contain undissolved particles that dissolve during the transfer process (termed secondary dissolution), resulting in inaccurate values for the dissolution rate. Another disadvantage of large-volume samples is that the vessel hydrodynamics are disrupted for the entire time the sample is being withdrawn from the vessel. For example, a typical transfer rate is 10 ml per minute, resulting in a full minute of disruption of the vessel hydrodynamics to withdraw a single 10-ml sample. In addition, withdrawing multiple large samples necessitates replenishing the sample media in the test vessel to maintain adequate volume for proper agitation of the mixture, adding complexity to the process.

Another disadvantage of prior art instruments is their inability to handle all possible dosage forms within a single test run or to handle the different dosage forms without modifying the instrument for each different dosage form. For example, some dosage forms, particularly capsules, float when placed into a fluid. These dosage forms must be inserted into "sinkers" that provide the needed additional weight to submerge the dosage form in the dissolution media. Alternatively, the dosage form may be inserted into a basket that is submerged in the dissolution media. Sinkers and tablets that sink can be placed directly into a dissolution vessel and agitated using a mixing paddle. The baskets themselves can be rotated or otherwise agitated, eliminating the need for a mixing paddle. Typically prior art systems are not able to handle tablets (and other dosage forms that are dispensed directly into the dissolution media) along with sinkers and baskets all within a single run. The dosage forms typically must be grouped by type and the instrument set up for that specific type of dosage form, often requiring modification of the system.

A dissolution testing system overcoming the aforementioned disadvantages is described in U.S. Pat. No. 8,158,059 B2. This system comprises multiple dissolution vessels and a dose carrier above the dissolution vessels. The dissolution vessels are arranged in a cylindrical tank having a circular cross section. The tank is filled with water for controlling the temperature inside the vessels.

However, a disadvantage of the known dissolution testing apparatus is that the vessels usually are difficult to monitor or to manipulate while they are arranged inside the tank. Even though in some applications the vessels are monitored by devices from the outside of the tank such monitoring is usually comparably cumbersome and nor appropriately precise. E.g., the devices around apparatus block the around space and the apparatus is less accessible and less visible. Or, e.g., the monitoring devices have to be placed in a well-defined position and orientation such that suitable results can be achieved.

Therefore, there is a need for a dissolution testing apparatus allowing a comparably precise monitoring of vessels inside a tank and/or an appropriate manipulation of the vessels inside the tank.

DISCLOSURE OF THE INVENTION

According to the invention this need is settled by an apparatus for dissolution testing comprising a tank which has a circular cylindrical outer body portion with a transparent side wall and a circular cylindrical inner body portion with a transparent side wall, wherein the inner body portion is essentially coaxially arranged in the outer body portion such that an outer interior having a ring-shaped cross section is defined between the outer body portion and the inner body portion and an inner interior having a circular cross section is defined inside the inner body portion. The apparatus further comprises a plurality of dissolution vessels arranged in the outer interior of the tank and a heater assembly arranged to heat test media in the vessels to a predefined temperature.

The plurality of dissolution vessels can comprise from four to ten vessels, from five to nine vessels or particularly from six to eight vessels. The predefined temperature can be about 37°±1° or particularly 37°±0.5°. The term "tank" in context of the invention relates to a container which can be filled with a fluid such as a heating liquid or which can be empty. The tank can have a fix bottom and a removable cover. The cover can be equipped with additional means for manipulating the vessels.

In the apparatus according to the invention free space is provided in direct vicinity of the vessels. In the free space means for monitoring and/or manipulating the vessels can be placed. Manipulating in this context can, e.g., relate to heating. Like this, it is possible to equip the apparatus with monitoring and/or manipulating means in precise relation to the vessels which means do not disturb by being placed around the apparatus. Also unintended movement or a derogation of these means can be prevented. The apparatus forms a compact unit in which these means can be integrated.

Thus, the apparatus according to the invention allows for a comparably precise monitoring of vessels inside the tank and/or an appropriate manipulation of the vessels inside the tank.

Preferably, the dissolution vessels are circularly arranged one besides another. In other words, the vessels inside the ring shaped or donut shaped outer interior of the tank can be regularly placed along a circle. Like this, it is possible to easily access all the vessels from the inner interior. Additionally, all vessels can be seen from the outside of the tank.

Furthermore, the position of the vessels can be precisely been defined. Thus, such arrangement allows for a precise and efficient monitoring and/or manipulation of the vessels.

Preferably, the apparatus comprises a test liquid agitating assembly arranged to agitate the test media inside the dissolution vessels. The test liquid agitating assembly can comprise stirrers for stirring media inside the vessels. Like this, agitation of the media inside the vessels can be provided which often is a prerequisite for dissolution testing.

Preferably, the apparatus comprises an optical monitoring assembly being arranged inside the inner interior of the tank. Such an optical monitoring system allows for efficiently and precisely monitoring the vessels. Thereby, the optical monitoring assembly preferably comprises a plurality of cameras each of which being directed to a different one of the dissolution vessels through the transparent side wall of the inner body portion of the tank. The number of cameras can correspond to the number of vessels. Like this, each vessel can individually efficiently be monitored.

Thereby, the optical monitoring assembly preferably comprises a support structure onto which the cameras are mounted. Such a support structure can allow for efficiently and precisely holding the cameras. Also, the mounting and demounting of the cameras can be comparably easy such that the cameras can efficiently be handled. Thereby, the support structure preferably comprises a plurality of holders and each of the cameras is mounted to one of the holders. The number of holders can correspond to the number of cameras. Thereby, the holders of the support structure are vertically movable for adjusting a height of the associated camera. Like this, the cameras can precisely be adjusted for covering the whole height of the vessels without requiring inappropriately losing the focus.

In a preferred embodiment, the heater assembly is arranged inside the inner interior of the tank. Like this, means suitable for heating the media in the vessels through the interior side wall can be placed in precise relation to the vessels. Thereby, the heater assembly preferably comprises a plurality of infrared lights each of which being directed to a different one of the dissolution vessels through the transparent side wall of the inner body portion of the tank. The number of infrared lights can correspond to the number of vessels. Such infrared light can be a means for precisely heating the media inside the vessels.

Thereby, the heater assembly preferably comprises a support structure with holders and each of the infrared lights is mounted to one of the holders. The number of holders can correspond to the number of infrared lights. Such a support structure can allow for efficiently and precisely holding the infrared lights. Also, the mounting and demounting of the lights can be comparably easy such that the lights can efficiently be handled, such as e.g. replaced. Thereby, the holders of the support structure preferably are vertically movable for adjusting a height of the associated infrared light. Like this, the media of the vessels can efficiently be heated over their whole height. Thereby, an insulation preferably is arranged in the outer interior of the tank.

In another preferred embodiment, the heater assembly comprises a continuous flow heater being connected with the outer interior of the tank. Such an arrangement allows for efficiently and precisely heating a liquid in the outer interior of the tank. By means of such a liquid the temperature of the media inside the vessels can be adjusted. Thereby, the heater assembly preferably comprises a pump being arranged to convey the liquid from the outer interior of the tank through the continuous flow heater back to the outer interior of the tank. Such a pump allows for an efficient conveying of the liquid which can be necessary for heating the liquid.

These and other aspects of the invention will be apparent from and elucidated with reference to the embodiment(s) described hereinafter.

BRIEF DESCRIPTION OF THE DRAWINGS

The apparatus according to the invention is described in more detail herein below by way of an exemplary embodiment and with reference to the attached drawings, in which.

DESCRIPTION OF EMBODIMENTS

In the following description certain terms are used for reasons of convenience and are not to be interpreted as limiting. The terms "right", "left", "up", "down", "under" and "above" refer to directions in the figures. The terminology comprises the explicitly mentioned terms as well as their derivations and terms with a similar meaning.

Figure 1:
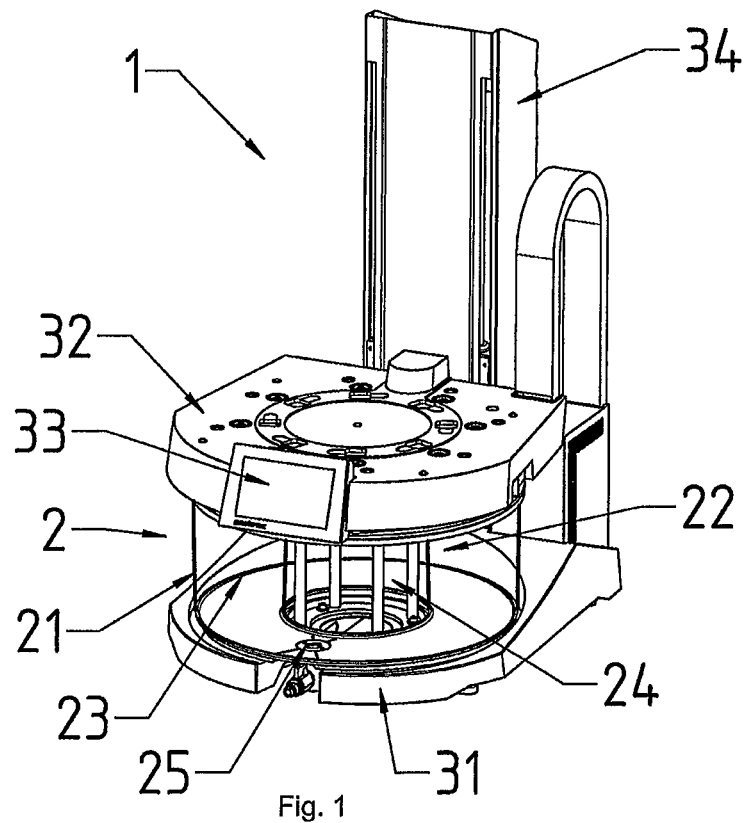
FIG. 1 shows a perspective view of a dissolution tester as an embodiment of an apparatus according to the invention.

FIG. 1 shows a dissolution tester 1 as an embodiment of an apparatus according to the invention. The dissolution tester 1 comprises a tank 2, a bottom 31 and a cover 32. The bottom has a plurality of feet on which it stands on a surface such as on a table or the like. The cover 32 covers the top side of the tank 2. It is mounted to a cover lift 34 by the means of which the cover 32 can be lifted from the tank 2 for accessing the interior of the tank 2. On a front side of the cover 32 a digital display is arranged for providing information about dissolution testing such as temperatures and the like. The tank 2 is releasably fixed on and supported by the bottom 31. The tank 2 comprised a circular cylindrical outer body portion 21 with a transparent side wall and a circular cylindrical inner body portion 22 also with a transparent side wall. The inner body portion 22 is coaxially arranged to the outer body portion 21. Thereby, an outer interior 23 having a ring-shaped cross section is defined between the outer body portion 21 and the inner body portion 22. An inner interior 24 having a circular cross section is defined inside the inner body portion 22. At the bottom of the outer interior 23 of the tank 2 a liquid outlet 25 is arranged.

The following applies to the rest of this description. If, in order to clarify the drawings, a figure contains reference signs which are not explained in the directly associated part of the description, then it is referred to previous description sections.

Figure 2:
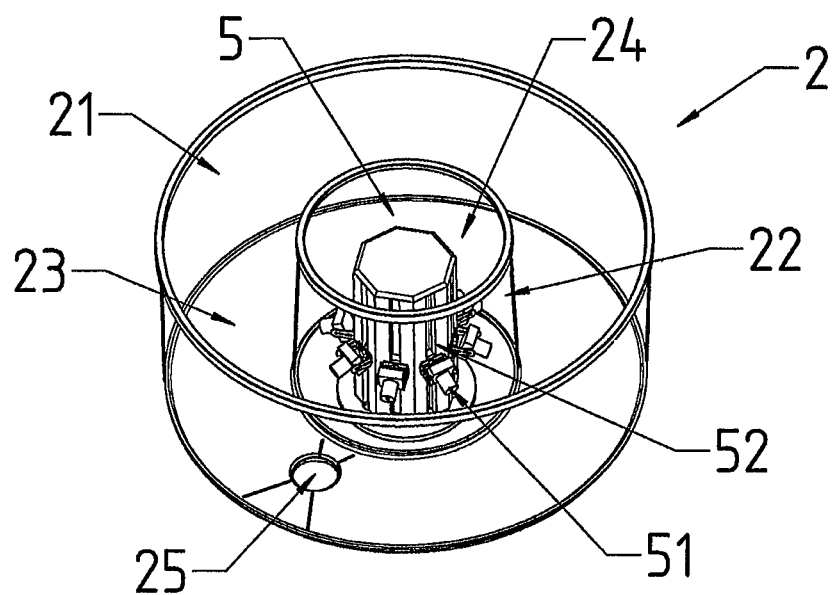
FIG. 2 shows a perspective view of a tank and a support pile of the dissolution tester of FIG. 1.
Figure 4:
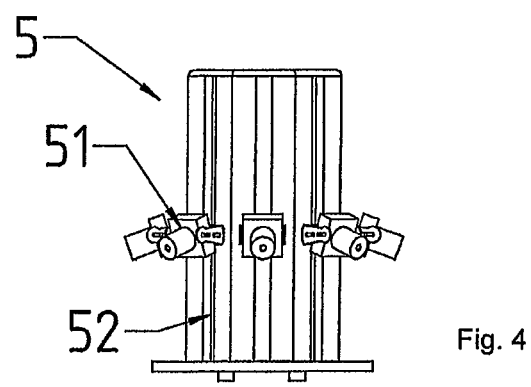
FIG. 4 shows a side view of the support pile of FIG. 3.

In FIG. 2 the tank 2 of the apparatus 1 is shown in more detail. Inside the inner interior 24 formed by the inner body portion 22 of the tank 2 a support pile 5 is arranged as support structure. As can also be seen in FIG. 4, the support pile 5 has vertical rails 52 into each of which a holder 51 is moveably mounted.

Figure 3:
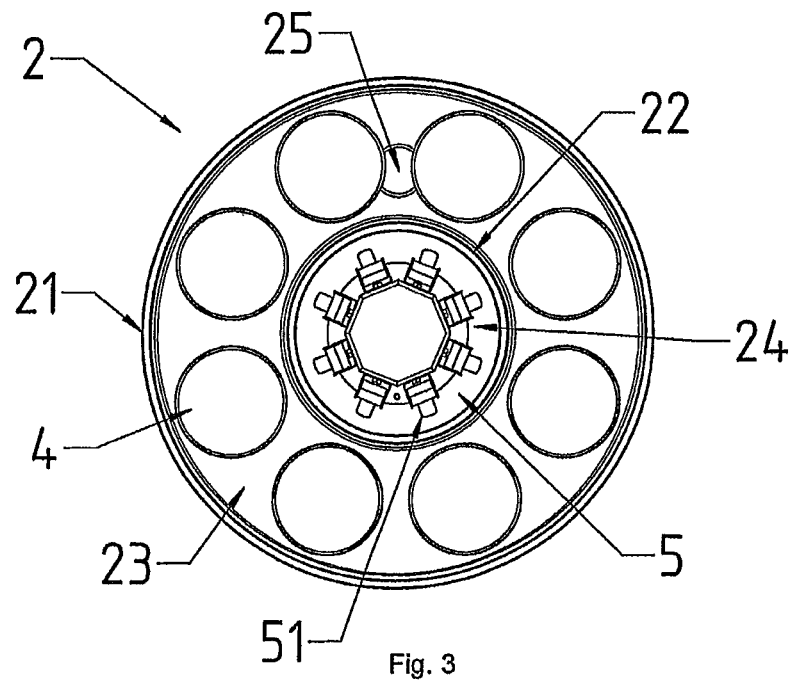
FIG. 3 shows a top view on the tank, the support pile and vessels of the dissolution tester of FIG. 1.
Figure 5:
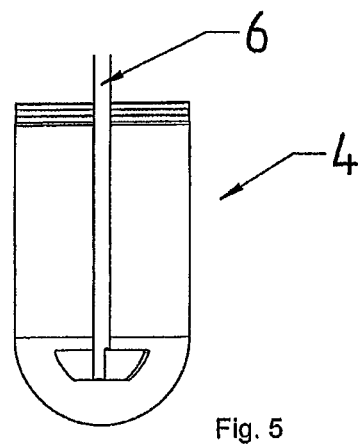
FIG. 5 shows a side view of one of the vessels of the apparatus of FIG. 1 with a stirrer.

FIG. 3 shows the tank 2 equipped with eight vessels 4. The vessels 4 are attached to an outer interior cap which covers the outer interior 23 of the tank 2 and which carries the vessels 4. Thereby, the vessels 4 are regularly arranged along a circle in the outer interior 23 of the tank 2. The support pile 5 has eight of the holders 51 wherein each holder 5 is associated to one of the vessels 4. As can be seen in FIG. 5, the vessels 4 are vials wherein a stirrer 6 is placed inside each of the vials. The stirrers 6 are comprised by a test media agitating assembly which is housed in the cover 32. Thus, by lifting the cover 32 from the tank 2 the stirrers 6 can be removed from the vessels 4 and vice versa.

For using the apparatus 1, the vessels 4 are provided with test media and the outer interior 23 with water as a heating media. To each of the holders 51 of the support pile 5 a camera is mounted which is directed to and monitoring one vessel 4. By arranging the outer interior cap with the vessels 4 onto the outer interior 23 of the tank 2, the vessels 4 are arranged inside the outer interior 23 of the tank 2 such that they are surrounded by the water. The outlet 25 of the outer interior 23 is connected to a continuous flow heater which heats the water inside the outer interior 23 in order to adjust the temperature of the test media inside the vessels 4 to about 37°. The tank 2 is then closed by the cover 32 wherein one of the stirrers 6 mounted to the cover 32 is arranged inside each of the vessels 4. During testing, the dissolution inside the vessels 4 can precisely be monitored by means of the cameras.

While the invention has been illustrated and described in detail in the drawings and foregoing description, such illustration and description are to be considered illustrative or exemplary and not restrictive. It will be understood that changes and modifications may be made by those of ordinary skill within the scope and spirit of the following claims. In particular, the present invention covers further embodiments with any combination of features from different embodiments described above and below. For example, it is possible to operate the invention in an embodiment wherein:

- The holders of the support pile can also be equipped with monitoring devices other than cameras.
- The holders of the support pile can also be equipped with a heating means such as an infrared light. Like this the test media inside the vessels can be heated by the heating means. In some embodiments it is not necessary to provide water into the outer interior of the tank and the liquid outlet as well as the continuous flow heater can be omitted.

The invention also covers all further features shown in the Figs. individually although they may not have been described in the afore or following description. Also, single alternatives of the embodiments described in the figures and the description and single alternatives of features thereof can be disclaimed from the subject matter of the invention or from disclosed subject matter. The disclosure comprises subject matter consisting of the features defined in the claims ort the exemplary embodiments as well as subject matter comprising said features.

Furthermore, in the claims the word "comprising" does not exclude other elements or steps, and the indefinite article "a" or "an" does not exclude a plurality. A single unit or step may fulfill the functions of several features recited in the claims. The mere fact that certain measures are recited in mutually different dependent claims does not indicate that a combination of these measures cannot be used to advantage. The terms "essentially", "about", "approximately" and the like in connection with an attribute or a value particularly also define exactly the attribute or exactly the value, respectively. The term "about" in the context of a given numerate value or range refers to a value or range that is, e.g., within 20%, within 10%, within 5%, or within 2% of the given value or range. Any reference signs in the claims should not be construed as limiting the scope.

The invention claimed is:

1. An apparatus for dissolution testing comprising:
    a tank having a circular cylindrical outer body portion with a transparent side wall and a circular cylindrical inner body portion with a transparent side wall, wherein the inner body portion is coaxially arranged with respect to the outer body portion such that an outer interior having a ring-shaped cross section is defined between the outer body portion and the inner body portion and an inner interior having a circular cross section is defined inside the inner body portion;
    a plurality of dissolution vessels arranged in the outer interior of the tank;
    the inner interior provides a free space wherein monitoring and/or manipulating assemblies for the dissolution vessels are placeable; and
    a heater assembly being arranged to heat a test media in the vessels to a predefined temperature.

2. The apparatus according to claim 1 wherein the dissolution vessels are circularly arranged one besides another.

3. The apparatus according to claim 1 comprising a test media agitating assembly arranged to agitate the test media inside the dissolution vessels.

4. The apparatus according to claim 1 comprising an optical monitoring assembly being arranged inside the free space of the inner interior of the tank.

5. The apparatus according to claim 4 wherein the optical monitoring assembly comprises a plurality of cameras each of which being directed to a different one of the dissolution vessels through the transparent side wall of the inner body portion of the tank.

6. The apparatus according to claim 5 wherein the optical monitoring assembly comprises a support structure onto which the cameras are mounted.

7. The apparatus according to claim 6 wherein the support structure comprises a plurality of holders and each of the cameras is mounted to one of the holders.

8. The apparatus according to claim 7 wherein the holders of the support structure are vertically movable for adjusting a height of the associated camera.

9. The apparatus according to claim 1 wherein the heater assembly is arranged inside the free space of the inner interior of the tank.

10. The apparatus according to claim 9 wherein the heater assembly comprises a plurality of infrared lights each of which being directed to a different one of the dissolution vessels through the transparent side wall of the inner body portion of the tank.

11. The apparatus according to claim 10 wherein the heater assembly comprises a support structure with holders and each of the infrared lights is mounted to one of the holders.

12. The apparatus according to claim 11 wherein the holders of the support structure are vertically movable for adjusting a height of the associated infrared light.

13. The apparatus according to claim 10 wherein an insulation is arranged in the outer interior of the tank.

14. The apparatus according to claim 1 wherein the heater assembly comprises a continuous flow heater being connected with the outer interior of the tank.

15. The apparatus according to claim 13 wherein the heater assembly comprises a pump being arranged to convey a liquid from the outer interior of the tank through the continuous flow heater back to the outer interior of the tank.

* * * * *